United States Patent [19]

Junek et al.

[11] 4,350,815
[45] Sep. 21, 1982

[54] PROCESS FOR THE PRODUCTION OF 4,6-DIAMINO-5-CYANO-3-ARYL-ISOXAZOLO [5,4-b] PYRIDINES

[75] Inventors: Hans Junek; Burkhard Thierrichter, both of Graz, Austria

[73] Assignee: Lonza Ltd., Gampel, Switzerland

[21] Appl. No.: 209,150

[22] Filed: Nov. 21, 1980

[30] Foreign Application Priority Data

Nov. 22, 1979 [CH] Switzerland .................. 10408/79

[51] Int. Cl.³ .......................................... C07D 498/04
[52] U.S. Cl. ..................................... 546/115; 546/116
[58] Field of Search ............................... 546/115, 116

[56] References Cited

U.S. PATENT DOCUMENTS

| | | | |
|---|---|---|---|
| 3,381,016 | 4/1968 | Markillic et al. | 260/296 |
| 3,736,325 | 5/1973 | Denzel et al. | 546/115 |
| 3,736,326 | 5/1973 | Denzel | 546/115 |
| 3,736,327 | 5/1973 | Denzel et al. | 546/115 |
| 3,825,535 | 7/1974 | Denzel et al. | 546/115 |
| 3,912,737 | 10/1975 | Denzel et al. | 546/115 |
| 3,985,760 | 10/1976 | Hoehn | 546/115 |

OTHER PUBLICATIONS

Quilico et al., Rend., Ist. Lombardo, Aci., 69, 1936, pp. 439 to 457.
Quilico et al., Gazz. Chim., Ital., 67, 1937, pp. 589 to 603.
Chemical Abstracts, vol. 78, (1973), 16162a.
Chemical Abstracts, vol. 80, (1974), 82964f.
Chemical Abstracts, vol. 85, (1976), 21450s.
Chemical Abstracts, vol. 84, (1976), 59279k.
Chemical Abstracts, vol. 73, (1973), 4236q.

*Primary Examiner*—John M. Ford
*Attorney, Agent, or Firm*—Fisher, Christen & Sabol

[57] ABSTRACT

Process for the production of 4,6-diamino-5-cyano-3-aryl-isoxazole [5,4-b] pyridines having the formula:

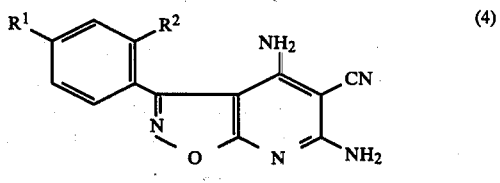

(4)

wherein (a) $R^1$ and $R^2$ are —H or (b) $R^1$ is —Cl and $R^2$ is —H, or (c) $R^1$ is —CH$_3$ and $R^2$ is —H or (d) $R^1$ is —NO$_2$ and $R^2$ is —H, or (e) $R^1$ is —H and $R^2$ is —NO$_2$. 2-Amino-1-propane-1,1,3-tricarbonitrile having the formula:

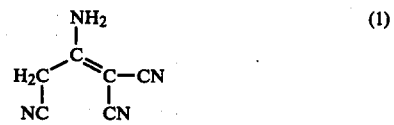

(1)

is reacted with a benzohydroxamino acid chloride having the formula:

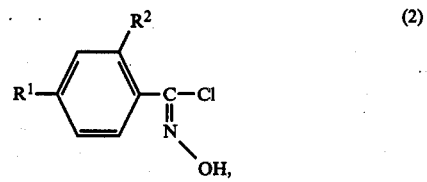

(2)

wherein $R^1$ and $R^2$ have the same meaning as above, in the presence of a strong base in at least a molar quantity.

9 Claims, No Drawings

PROCESS FOR THE PRODUCTION OF 4,6-DIAMINO-5-CYANO-3-ARYL-ISOXAZOLO [5,4-b] PYRIDINES

BACKGROUND OF THIS INVENTION

1. Field of this Invention

This invention involves the production of isoxazolo [5,4—b] pyridines.

2. Prior Art

Various processes for the synthesis of isoxazolo [5,4—b] are known. Two of such processes start out with 5-amino-isoxazoles, which are cyclized with β-ketoesters of 1,3-diketones (U.S. Pat. No. 3,381,016) or are reacted with alkoxy methylene malonic or acetic acid esters into enamines and are subsequently subjected by heating in diphenyl ether or polyphosphoric acid to cyclization. [(T. Denzel and H. Hoehn, Arch. Pharmaz. 305, 833 (1972), and W. Janssen and T. Denzel, Arch. Pharmaz. 308, 471 (1975)].

Benzohydroxyamino acid chlorides were used for the first time as starting compounds for the production of isoxazoles by Quilico et al., Rend. ist. lombardo sci. 69, 439 (1936), and Quilico et al., Gazz. chim. ital. 67, 589 (1937), in the case of reaction with β-diketones, β-ketoaldehydes, β-ketoesters, malonic esters, cyano acetic ester and cyano ketones. It is particularly mentioned that the reactions with cyano acetamide and cyano acetic ester lead to 3,4,5-trisubstituted isoxazoles.

BROAD DESCRIPTION OF THIS INVENTION

An object of this invention is to provide for the production of 4,6-diamino-5-cyano-3-aryl-isoxazolo [5,4—b] pyridines in a simple manner. Other objects and advantages of this invention are set out herein or are obvious herefrom to one ordinarily skilled in the art.

The objects and advantages of this invention are achieved by the process of this invention.

This invention involves a process for production of 4-6-diamino-5-cyano-3-aryl-isoxazolo [5,4—b] pyridines having the formula:

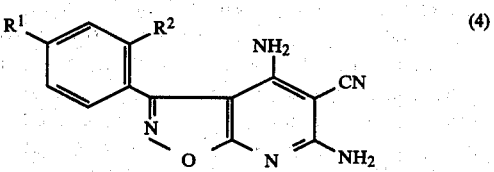

wherein (a) $R^1$ and $R^2$ are —H, or (b) $R^1$ is —Cl and $R^2$ is —H, or (c) $R^1$ is —CH$_3$ and $R^2$ is —H, or (d) $R^1$ is —NO$_2$ and $R^2$ is —H, or (e) $R^1$ is —H and $R^2$ is —NO$_2$. 2-Amino-1-propane-1,1,3-tricarbonitrile having the formula:

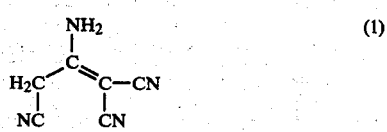

is reacted with a benzohydroxyamino acid chloride having the formula:

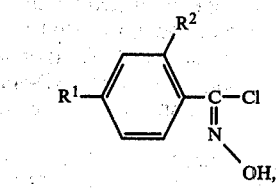

wherein $R^1$ and $R^2$ have the same meaning as above, in the presence of a strong base, used in at least a molar quantity (strength).

Preferably the strong base is sodium methylate or aqueous sodium hydroxide. Preferably the reaction is conducted at a temperature of —10° to +50° C. Preferably the reaction is conducted in water or an alcohol. More preferably the reaction is conducted in methanol or ethanol. Preferably 10 to 25 ml. of the solvent or suspending agent is used per gram of starting material.

By way of summary, this invention involves a process for the production of 4,6-diamino-5-cyano-3-aryl-isoxazolo [5,4—b] pyridines from 2-amino-1-propane-1,1,3-tricarbonitrile and benzobenzohydroxyamino acid in the presence of a strong base.

This invention also includes the intermediates and end products.

DETAILED DESCRIPTION OF THIS INVENTION

Any suitable strong base can be used. Examples of useful alkali metal and alkaline earth metal carbonate basic agents are sodium carbonate, potassium carbonate, magnesium carbonate, cesium carbonate, barium carbonate, radium carbonate, calcium carbonate, strontium carbonate, beryllium carbonate, rubidium carbonate and lithium carbonate. Another useful carbonate is ammonium carbonate. Examples of useful alkali metal and alkaline earth hydroxide basic agents are sodium hydroxide, potassium hydroxide, magnesium hydroxide, calcium hydroxide, barium hydroxide, strontium hydroxide, beryllium hydroxide, cesium hydroxide and lithium hydroxide. Another useful hydroxide is ammonium hydroxide. Examples of useful alkali metal or alkaline earth metal alcoholates or alkoxides basic agents are sodium methoxide, sodium ethoxide and magnesium methoxide. Examples of useful alkali metal or alkaline earth metal oxide basic agents are sodium monoxide, potassium monoxide, potassium monoxide, magnesium oxide, barium oxide, strontium oxide, calcium oxide, berylium oxide, cesium oxide, rubidium oxide and lithium oxide. The preferred strong bases are sodium methylate or ethylate dissolved in methanol, ethanol, and aqueous sodium hydroxide. (Sodium methylate is sodium methoxide and sodium ethylate is sodium ethoxide.) Mixtures of bases can be used.

The reaction temperature is preferably maintained at ambient temperatures; a temperature of —10° to +50° C. is suitable for the process of this invention.

The reaction can be carried out in water or an alcohol, for examples, a $C_1$ to $C_4$ alcohol, such as, methanol, ethanol, propanol, isopropanol and butanol. Methanol and ethanol are the preferred alcohols. The quantity of solvent or suspension agent is not critical; preferably 10 to 25 ml of solvent or suspending agent per gram of starting material is used. Mixtures of solvents and/or suspending agents can be used.

Whenever 2-amino-1-propene-1,1,3-tricarbonic nitrile (1) and phenyl hydroxyamino acid chloride (2a) are reacted in the presence of sodium methylate as a starting base at a temperature below 15° C., then 3-amino-2-cyano-3-(5-amino-3-phenyl-isoxanole-4-yl)-acrylonitrile (3a) can be isolated as the intermediate product. The intermediate product on its part can then be reacted with caustic soda solution at 50° to 100° C. to produce 4,6-diamino-5-cyano-3-phenyl-isoxazolo [5,4—b] pyridine (4a). By diazotizing and boiling down with $HNO_2$, 4-amino-5-cyano-3-phenyl-isoxazole [5,4—b] pyridine can be converted into 4-amino-6-hydroxy-3-phenyl-isoxazolo [5,4—b] pyridine-5-carbonitrile (5a).

The reaction of this invention thus follows the following formula (reaction path), wherein:
in the
a formulas is: $R^1$=—H, $R^2$=—H
b formulas is: $R^1$=—Cl, $R^2$=—H
c formulas is: $R^1$=—$CH_3$, $R^2$=—H
d formulas is: $R^1$=—$NO_2$, $R^2$=—H
e formulas is: $R^1$=—H, $R^2$=—$NO_2$

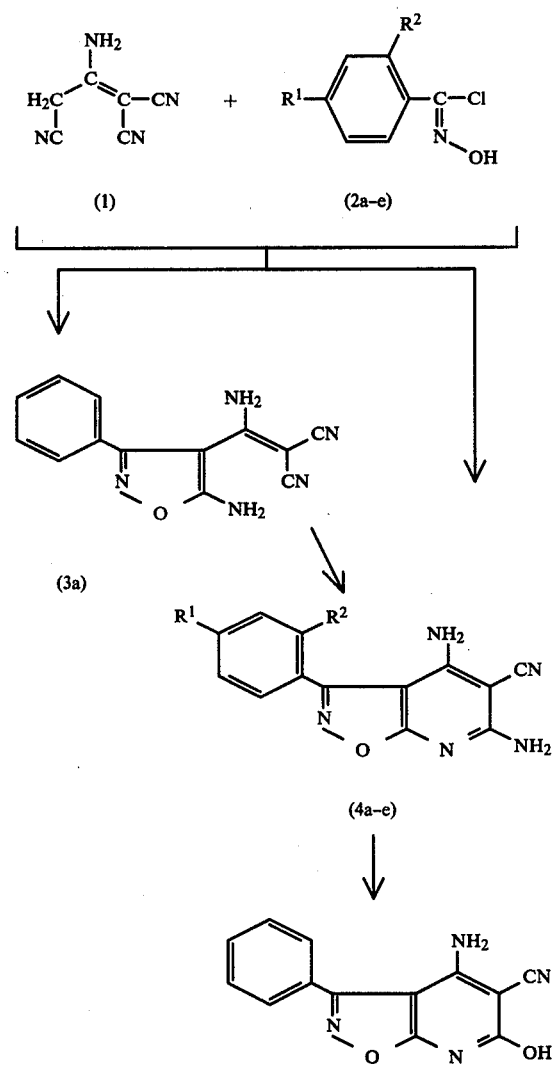

The products of this invention, namely the 4,6-diamino-5-cyano-3-phenylisoxazolo [5,4—b] pyridines and its companion 4b—e compounds, and 4-amino 6-hydroxy-3-phenyl-isoxazolo [5,4—b] pyridine-5-carbonitrile are useful as a tranquilizer, an antiinflammatory agent, an antiasthamatic (Chemical Abstracts 78, 4236Q, 4235P and 16162A, Chemical Abstracts 80, 82964F, and Chemical Abstracts 85, 21450S) or for plant grow regulation (Chemical Abstracts 84, 59279K). Also utility by analogy is involved.

This invention also includes compounds 4b—e which have the formula:

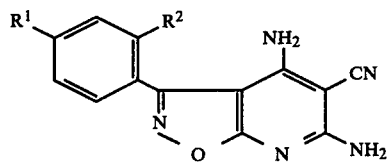

wherein:
4b is: $R^1$=—Cl, $R^2$=H
4c is: $R^1$=—$CH_3$, $R^2$=H
4d is: $R^1$=—$NO_2$, $R^2$=H
4e is: $R^1$=—H, $R^2$=$NO_2$

EXAMPLE 1

4,6-Diamino-5-cyano-3-aryl-isoxazolo [5,4—b] pyridine (4a—e)

4a: 0.7 g (5 mmole) of compound (1) and 1.0 g (6.45 mmole) of compound (2a) are shaken in 10 ml of 2 N NaOH for 2 minutes at ambient temperature. The reaction mixture is mixed with 10 ml of $H_2O$, and the precipitate is sucked off (removed) and contacted with diluted NaOH. The yield was 0.4 g (32 percent) of colorless prisms, from glacial acetic acid, having a melting point of 280° C.

For the production of compounds (4b to 4e) one proceeds analogously, but instead of NaOH, sodium methylate solution can also be used. For the analytical and spectroscopic data see Tables 1 and 2 below.

EXAMPLE 2

3-Amino-2-cyano-3-(5-amino-phenyl-isoxazole-4-yl)-acrylonitrile (3a)

A suspension of 1.3 g (10 mmole) of compound (1) in 15 ml of absolute ethanol is added to a freshly prepared sodium methylate solution (0.23 g of Na in 15 ml of EtOH) while stirring. The reaction mixture is cooled to −5° C. To this a solution 0.7 g (11 mmole) of compound (2a) in 8 ml of EtOH is added drop by drop, so that the temperature does not rise above 15° C. Then after 1 hour, the solution is stirred again. The precipitate is sucked off (removed), digested with acetic acid and sucked off (removed once more. The yield was 2.0 g (80 percent) of yellow bars, from nitrobenzene, having a melting point of 300° C. Data concerning the product is:

| | $C_{13}H_9N_5O$ (251.2) | | |
|---|---|---|---|
| | C, percent | H, percent | N, percent |
| Calc.: | 62.15 | 3.61 | 27.87 |
| Found: | 62.18 | 3.63 | 27.93 |

IR(KBr): 3470, 3360, 3240 ($NH_2$), 2205 (HN), 1635, 1590 (C=C) $cm^{-1}$.

EXAMPLE 3

4,6-Diamino-5-cyano-3-phenyl-isoxazolo [5,4—b] pyridine (4a)

0.5 g (2 mmole) of compound (3a) is dissolved in 20 ml of 2 N NaOH, and heated to boiling for 5 minutes. After cooling, the precipitate is sucked off (removed). The yield is 0.25 g (50 percent) of colorless needles, from glacial acetic acid.

EXAMPLE 4

4-Amino-6-hydroxy-3-phenyl-isoxazolo [5,4—b] pyridine-5-carbonitrile (5a)

0.4 g (1.59 mmole) of 3,6-diamino-5-cyano-3-phenyl-isoxazolo [5,4—b] pyridine (4a) is dissolved in 25 ml of 6 N HCl in heat. Then 5 ml of $H_2O$ is added and mixed drop by drop with a solution of 0.4 g of $NaNO_2$ in 5 ml of $H_2O$. The solution is heated to boiling for 60 minutes. The precipitate is sucked off (removed) hot. The yield is 0.2 g (50 percent) of colorless plates, from glacial acetic acid, having a melting point of 251° C.

For the production of compounds (5b to 5e) one proceeds analogously.

TABLE I

Isoxazolo-pyridine (4a–e) Product Analytical Data

| -isoxazolo [5,4-b] pyridine (Compound 4) | Percent Yield; Melt. Point, °C. | Sum-Formula (Mole Mass) | Recrystal- lized From | | Analysis | | | |
|---|---|---|---|---|---|---|---|---|
| | | | | | C | H | N | Cl |
| a 4,6-Diamino-5-cyano 3-phenyl | 32 280 | $C_{13}H_9N_5O$ (251.2) | Glacial Acetic Acid | Calc. Found | 62.15 62.50 | 3.61 3.68 | 27.87 27.07 | |
| b 3-(p-Chlorophenyl)-4,6- diamino-5-cyano | 42 300 | $C_{13}H_8N_5OCl$ (285.7) | Nitrobenzene | Calc. Found | 54.65 54.72 | 2.82 2.81 | 24.52 24.09 | 12.41 12.11 |
| c 4,6-Diamino-5-cyano 3-(p-tolyl) | 69 300 | $C_{14}H_{11}N_5O$ (265.3) | Nitrobenzene | Calc. Found | 63.38 63.51 | 4.18 4.20 | 26.41 26.56 | |
| d 4,6-Diamino-5-cyano- 3-(p-nitrophenyl) | 37 300 | $C_{13}H_8N_6O_3$ (296.2) | Nitrobenzene | Calc. Found | 52.71 51.65 | 2.72 2.77 | 28.37 28.16 | |
| e 4,6-diamino-5-cyano- 3-(o-nitrophenyl) | 75 290 | $C_{13}H_8N_6O_3$ (296.2) | Dioxane/$H_2O$ | Calc. Found | 52.71 52.95 | 2.72 2.82 | 28.37 28.37 | |

Spectroscopic Data (IR-Spectra And Mass Spectra) For Compounds (4a to 4e)

| Characteristic, —$NH_2$ | IR-Bands, —CN | ($cm^{-1}$) In KBr, —C=C | MS-Data;m/e - Values (Percent) |
|---|---|---|---|
| a 3450, 3340 | 2200 | 1630, 1600 | — |
| b 3460, 3360, 3220 | 2210 | 1640, 1590 | — |
| c 3450, 3340, 3210 | 2200 | 1635, 1600 | 265 (62), 264 (80), 249 (10), 237 (12), 221 (11), 209 (10), 194 (40), 148 (37), 120 (35), 91 (100). |
| d 3460, 3350, 3210 | 2210 | 1640, 1590 | — |
| e 3460, 3340, 3210 | 2200 | 1635, 1595 | 296 (53), 266 (3), 250 (8), 195 (10), 176 (30), 148 (100), 120 (85). |

What is claimed is:

1. Process for the production of a 4,6-diamino-5-cyano-3-arylisoxazolo [5,4—b] pyridine having the formula:

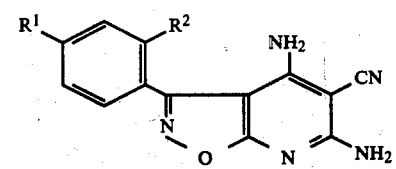

(4)

wherein (a) $R^1$ and $R^2$ are —H, or (b) $R^1$ is —Cl and $R^2$ is —H, or (c) $R^1$ is —$CH_3$ and $R^2$ is —H, or (d) $R^1$ is —$NO_2$ and $R^2$ is —H, or (e) $R^1$ is —H and $R^2$ is —$NO_2$, comprising reacting 2-amino-1-propane-1,1,3-tricarbonitrile having the formula:

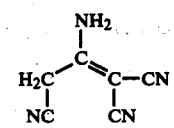

(1)

with a benzohydroxyamino acid chloride having the formula:

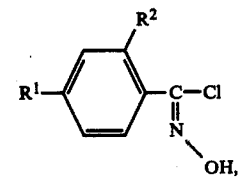

(2)

wherein $R^1$ and $R^2$ have the same meaning as above, in the presence of a strong base used in a form of at least a molar quantity.

2. Process claimed in claim 1 wherein the strong base is sodium methylate in methanol or aqueous sodium hydroxide.

3. Process as claimed in claim 1 wherein the reaction is conducted at a temperature of —10° to +50° C.

4. Process as claimed in claim 1 wherein the reaction is conducted in water or an alcohol.

5. Process as claimed in claim 1 wherein 10 to 25 ml. of the solvent or suspending agent is used per gram of starting material (1).

6. Process as claimed in claim 1 wherein the reaction is conducted in methanol or ethanol.

7. Process for producing 4-amino-6-hydroxy-3-phenylisoxazolo [5,4—b] pyridine-5-carbonitrile having the formula:

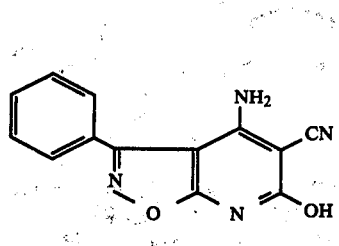

which comprises diazotizing the product of claim 1 and then boiling down the diazotized product of claim 1 with $HNO_2$.

8. 4,6-diamino-5-cyano-3-phenyl-isoxazolo [5,4—b] pyridine having the formula:

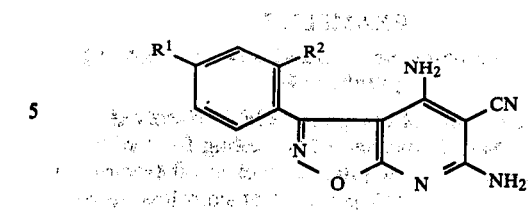

wherein (a) $R^1$ and $R^2$ are —H, or (b) $R^1$ is —Cl and $R^2$ is —H, or (c) $R^1$ is —$CH_3$ and $R^2$ is —H or (d) $R^1$ is —$NO_2$ and $R^2$ is —H, or (e) $R^1$ is —H and $R^2$ is —$NO_2$.

9. 4-Amino-6-hydroxy-3-phenyl-isoxazolo [5,4—b] pyridine-5-carbonitrile having the formula:

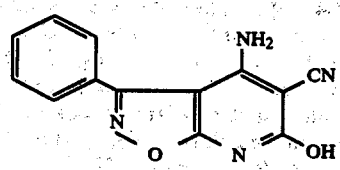

* * * * *